(12) United States Patent
Morningstar

(10) Patent No.: US 7,942,808 B1
(45) Date of Patent: May 17, 2011

(54) METHOD OF IMPLANTING A PENILE PROSTHESIS

(75) Inventor: Randy L. Morningstar, Brooklyn Park, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 12/868,737

(22) Filed: Aug. 26, 2010

(51) Int. Cl.
*A61F 13/00* (2006.01)

(52) U.S. Cl. .......................................................... 600/40

(58) Field of Classification Search .............. 600/38–41; 128/897, 898
See application file for complete search history.

(56) References Cited

U.S. PATENT DOCUMENTS

| 4,628,912 | A | | 12/1986 | Fischell | |
| 5,010,882 | A | * | 4/1991 | Polyak et al. | 600/40 |
| 5,782,865 | A | | 7/1998 | Grotz | |
| 6,808,489 | B2 | * | 10/2004 | George et al. | 600/40 |
| 2001/0018597 | A1 | | 8/2001 | Gellman | |

* cited by examiner

*Primary Examiner* — Samuel G Gilbert
(74) *Attorney, Agent, or Firm* — Coloplast Corp., Coloplast A/S; Daniel G. Chapik; Nicholas R. Baumann

(57) ABSTRACT

A method of providing a patient having a predetermined corporotomy length with an implant having a length that is sized for the predetermined corporotomy length is disclosed. The method includes providing a penile implant having a delivered length that is approximately equal to the predetermined corporotomy length and comprising a distance that extends from a distal end of a distal tip to a proximal end of a proximal tip assembly, the proximal tip assembly providing a first proximal tip diameter. The method additionally includes reducing the first proximal tip diameter to a smaller implantable proximal tip diameter.

5 Claims, 7 Drawing Sheets

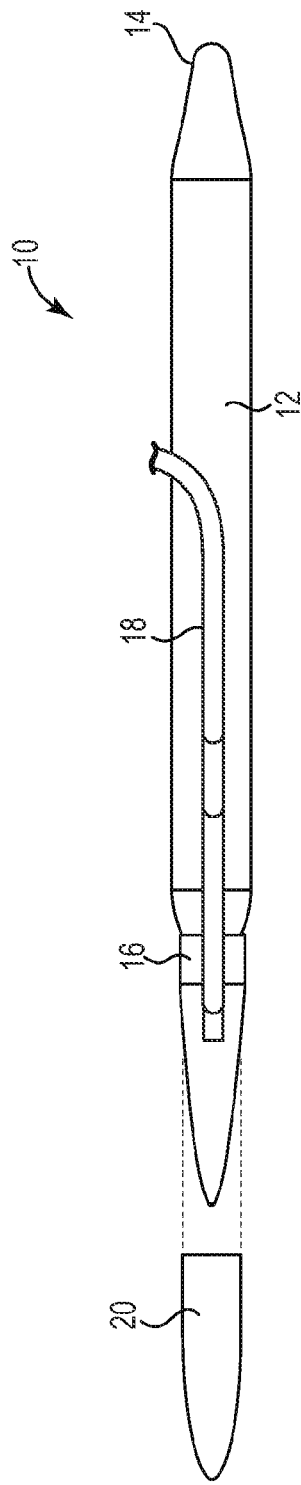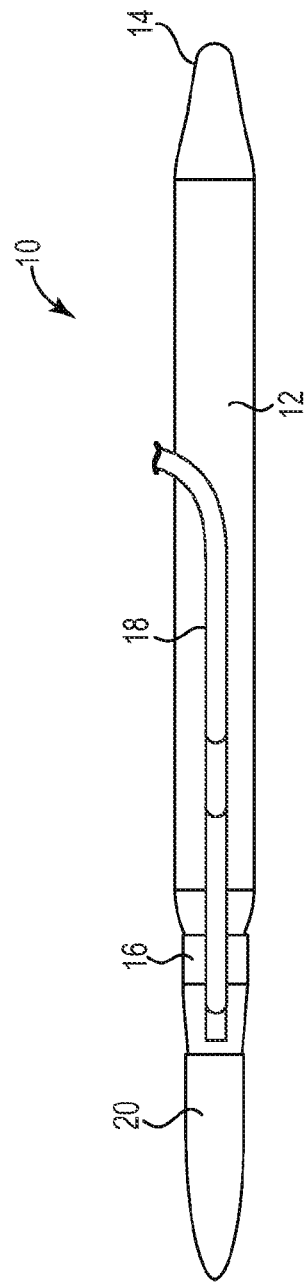
Fig. 1A
PRIOR ART
Fig. 1B
PRIOR ART

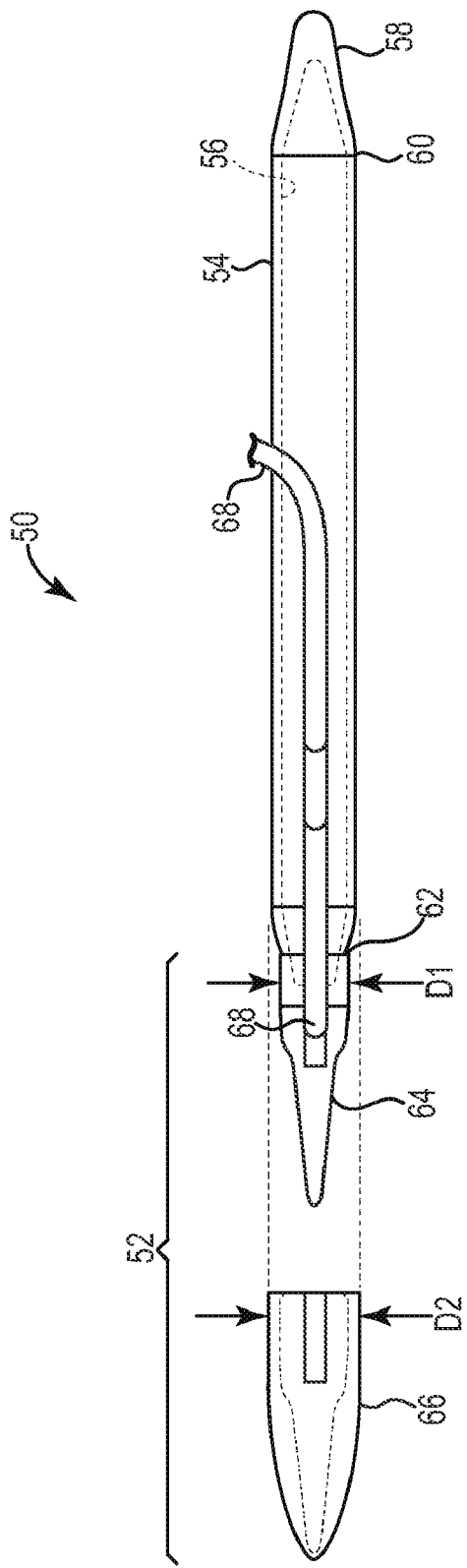

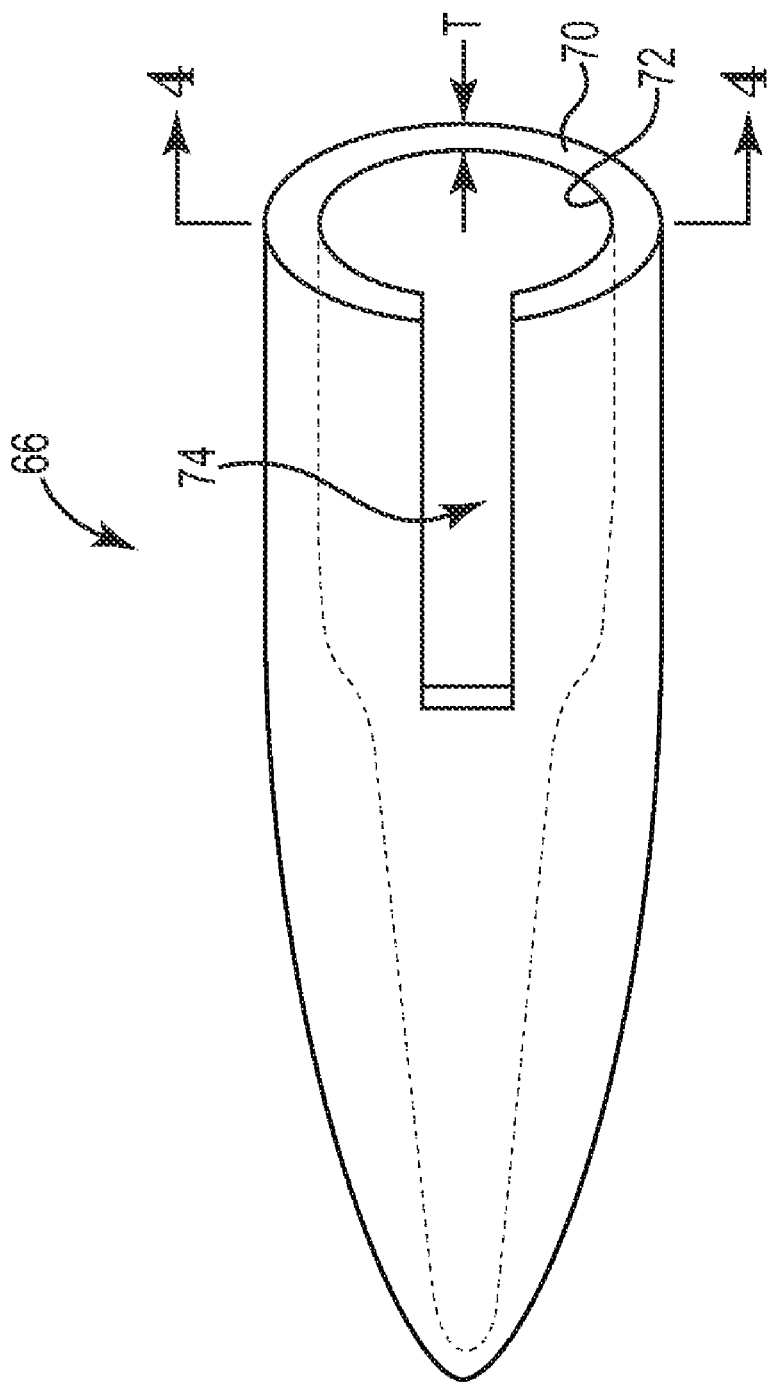

METHOD OF IMPLANTING A PENILE PROSTHESIS

BACKGROUND

Penile implants provide relief for men with erectile dysfunction. In a typical implantation procedure, the penis of the patient is incised to expose two corpora cavernosa that are aligned axially in a side-by-side orientation within the penis. A corporotomy is formed that is sized to receive the penile implant. For example, each corpora cavernosum is dilated proximally towards a crus of the penis and distally into the glans penis in a corporotomy procedure by introducing gradually larger stainless steel rods into the corpora cavernosum. The corporotomy thus has a length that extends between the crus of the penis and the glans penis. The proximal portion of the corporotomy has a diameter that is approximately the diameter of the largest stainless steel rod that the surgeon was able to insert into the corpora cavernosum. A penile implant is selected that most nearly matches the length of the corporotomy and a diameter that most nearly matches the diameter of the proximal portion of the corporotomy.

Although the above-described approach has proven effective in treating erectile dysfunction, the variety of different length and diameter penile implants maintained in the inventory of the hospital can be prohibitively expensive.

SUMMARY

One aspect provides a penile implant including an inflatable bladder providing a fluid chamber, a distal tip extending from a distal end of the inflatable bladder, and a proximal tip assembly extending from a proximal end of the inflatable bladder. The proximal tip assembly includes a tip core providing a first proximal tip diameter and a tip sleeve disposed over the tip core to provide a second proximal tip diameter that is larger than the first proximal tip diameter. The tip sleeve is removable from the tip core to provide the penile implant with a proximal tip that is convertible between the first and second proximal tip diameters.

One aspect provides a method of providing a patient having a predetermined corporotomy length with an implant having a length that is sized for the predetermined corporotomy length. The method includes providing a penile implant having a delivered length that is approximately equal to the predetermined corporotomy length and comprising a distance that extends from a distal end of a distal tip to a proximal end of a proximal tip assembly, the proximal tip assembly providing a first proximal tip diameter. The method additionally includes reducing the first proximal tip diameter to a smaller implantable proximal tip diameter.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1A is an exploded side view and FIG. 1B is an assembled side view of a conventional penile implant.

FIG. 2 is a side view of one embodiment of a penile implant with a proximal tip assembly having a tip sleeve that converts the proximal tip of the implant from a first narrower diameter to a second larger diameter.

FIG. 3 is a perspective view of one embodiment of the tip sleeve illustrated in FIG. 2.

DETAILED DESCRIPTION

Figure 4:
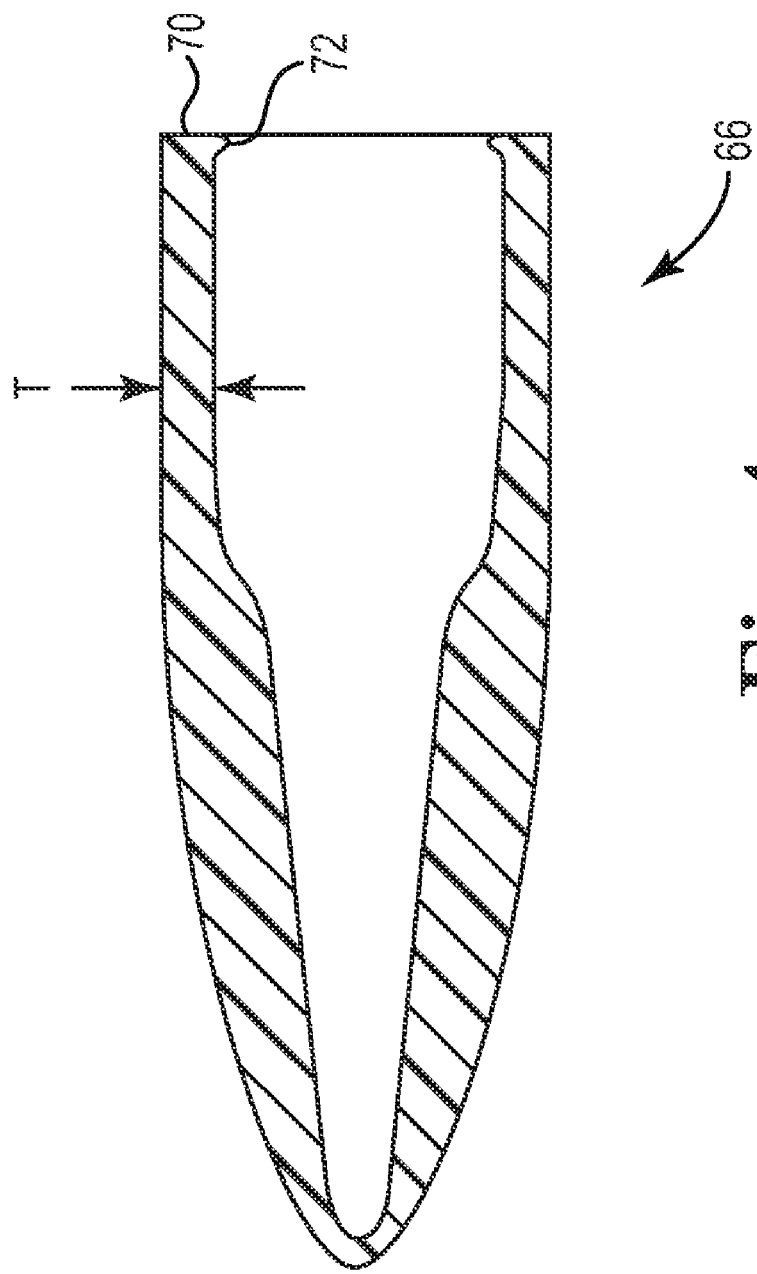
FIG. 4 is a side cross-sectional view of the tip sleeve illustrated in FIG. 3.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Soft tissue includes dermal tissue, sub-dermal tissue, ligaments, tendons, or membranes but does not include bone.

The term "proximal" as employed in this application means that part that is situated next to or near the point of attachment or origin or a central point: as located toward a center of the human body. The term "distal" as employed in this application means that part that is situated away from the point of attachment or origin or the central point: as located away from the center of the human body. A distal end is the furthest endmost location of a distal portion of a thing being described, whereas a proximal end is the nearest endmost location of a proximal portion of the thing being described. For example, the glans penis is located distal and of the crus of the penis is located proximal relative to the male body such that a distal end of a corpora cavernosum of the patient extends about midway into the glans penis.

FIG. 1A is an exploded side view and FIG. 1B is an assembled side view of a conventional penile implant 10. The conventional penile implant 10 includes an inflatable cylinder 12 having a distal tip 14, a proximal tip 16, tubing 18 attached to the proximal tip 16 to inflate the inflatable cylinder 12 with liquid, and a rear tip extender 20 that is attachable to the proximal tip 16.

During an implantation procedure, the surgeon employs a tool to form an opening (a corporotomy) in the soft tissue of the corpora cavernosa of the penis. The corporotomy extends in a proximal direction into the patient toward a crus of the penis and a distal direction toward the glans penis. The surgeon measures the length of the corporotomy extending between the crus and the glans penis and selects one of the above-described conventional penile implants 10 having a length that most nearly approximates the measured length of the corporotomy. In some cases, the nearest length of the selected implant 10 is shorter than the measured length of the corporotomy and the surgeon will add one or more "rear tip" extenders to lengthen the conventional penile implant 10.

Patients have different anatomical sizes. It is desirable to provide the conventional penile implant 10 with one or more rear tip extenders 20 (RTEs 20) that offer additional length to better fit patients with longer proximal corpora. To this end, the rear tip extender 20 is provided in a variety of lengths from about 1-12 cm and is attachable to the proximal tip 16 to extend an overall length of the conventional penile implant 10.

The RTEs 20 are attached to the penile implant 10 to add length to the implant 10 and have a diameter that is always less that a diameter of the implant 10. The RTEs 20 do not allow the surgeon to scale the selected conventional penile implant 10 down to a suitable narrower proximal diameter since the RTEs 20 lengthen the conventional penile implant 10 without changing its diameter. Thus, RTEs 20 attached to the conventional penile implant 10 do not provide a solution if the surgeon determines that the proximal portion of the corpora is narrower than the corporotomy, for example due to fibrotic tissue growth or other physical characteristics.

Embodiments provide a proximal tip assembly that extends from a proximal end of an inflatable bladder of a penile implant. The proximal tip assembly has a tip core that provides a first proximal tip diameter and a tip sleeve disposed over the tip core that provides a second proximal tip diameter that is larger than the first proximal tip diameter. The tip sleeve is removable from the tip core to provide the penile implant with a proximal tip that is convertible between the first and second proximal tip diameters to allow the surgeon to selectively scale the implant to accommodate a proximal portion of the corpora that is narrower than the remaining corporotomy. Thus, in contrast to the conventional implant 10 with an RTE 20 that is attached to the penile implant 10 to add length, embodiments described herein provide a tip sleeve that is removable from a rear tip of a penile implant to provide an implant having a narrower implantable proximal tip.

Embodiments provide an implant having a delivered proximal tip diameter that will accommodate a corporotomy having an approximately uniform diameter by allowing the surgeon to employ the proximal tip assembly with the tip sleeve in place over the tip core, and alternatively, that will accommodate a proximal portion of the corpora that is narrower than the remaining corporotomy by removing the tip sleeve from the tip core to present an implantable proximal tip diameter that is smaller than the delivered proximal tip diameter.

FIG. 2 is a side view of one embodiment of a penile implant 50 provided with a convertible proximal tip assembly 52. The penile implants 50 includes an inflatable bladder 54 providing a fluid chamber 56, a distal tip 58 extending from a distal and 60 of the inflatable bladder 54, where the proximal tip assembly 52 extends from a proximal and 62 of the inflatable bladder 54. The proximal tip assembly 52 includes a tip core 64 that provides a first proximal tip diameter D1 and a tip sleeve 66 disposed over the tip core 64 to provide a second proximal tip diameter D2 that is larger than D1. The tip sleeve 66 is removable from the tip core 64 to provide the implant of 50 with a proximal tip that is convertible between the first and second proximal tip diameters D1, D2. Tubing 68 is attached to the proximal tip assembly 52 and communicates with the fluid chamber 56. The tubing 68 provides a conduit 68 that communicates with a fluid reservoir (not shown), where the fluid reservoir provides a repository for the fluid that is employed to inflate the inflatable bladder 54.

The inflatable bladder 54 is generally provided as an oblong cylinder that is closed and sealed and thus configured to be inflated when fluid (e.g., saline typically, or a gas) is introduced into the tubing 68. In general, it is desirable to deflate the inflatable bladder 54 in preparation for implantation of the implant 50 into the penis, since the deflated bladder 54 is easier to insert into the corporotomy formed in the corpora cavernosum. The bladder 54 is configured to be subsequently inflated by the surgeon to ensure performance of implant 50, and later after healing by the patient to achieve an erection.

In one embodiment, the inflatable bladder 54 is fabricated from a urethane material sold under the trademark Bioflex and is available from Coloplast Corp., Minneapolis, Minn.

The distal tip 58 is attached to the distal end 60 of the inflatable bladder 54. In one embodiment, the distal tip 58 is formed from silicone, which is dissimilar to the urethane material of the Bioflex inflatable bladder 54. To facilitate the attachment of these two dissimilar materials, in one embodiment the urethane material of the inflatable bladder 54 is coated with fumed silica to prepare the urethane surface for bonding with the silicone tip 58. Alternatively, in one embodiment the distal tip 58 is integrally formed to extend from the distal end 60 of the inflatable bladder 54 as a one-piece unit.

The proximal tip core 64 is attached to the proximal end 62 of the inflatable bladder 54. In one embodiment, the tip core 64 is fabricated from silicone and is permanently connected to the proximal end 62 two of the inflatable bladder 54.

In one embodiment, the distal tip 58 and the proximal tip core 64 are integrally formed with the inflatable bladder 54 to provide a monolithic penile prosthesis, where the tip sleeve 66 is removable from the monolithic penile prosthesis.

FIG. 3 is a perspective view and FIG. 4 is a cross-sectional view of the tip sleeve 66. In one embodiment, a distal end 70 of the tip sleeve 66 provides an attachment ring 72 that is sized to seat and engage around a distal end of the proximal tip core 64. In one embodiment, the tip sleeve 66 forms a recess 74 extending in a proximal direction from the distal end 70 that is sized to receive the conduit 68 when the attachment ring 70 is engaged around the proximal tip core 74. The tip sleeve 66 is formed to have a thickness T such that the diameter D2 is greater than the diameter D1 by a factor of 2T. In one embodiment, the thickness T is between approximately 0.5-2 mm. The tip sleeve 66 is suitably fabricated from a polymer material, one suitable example of which is silicone.

Figure 5:
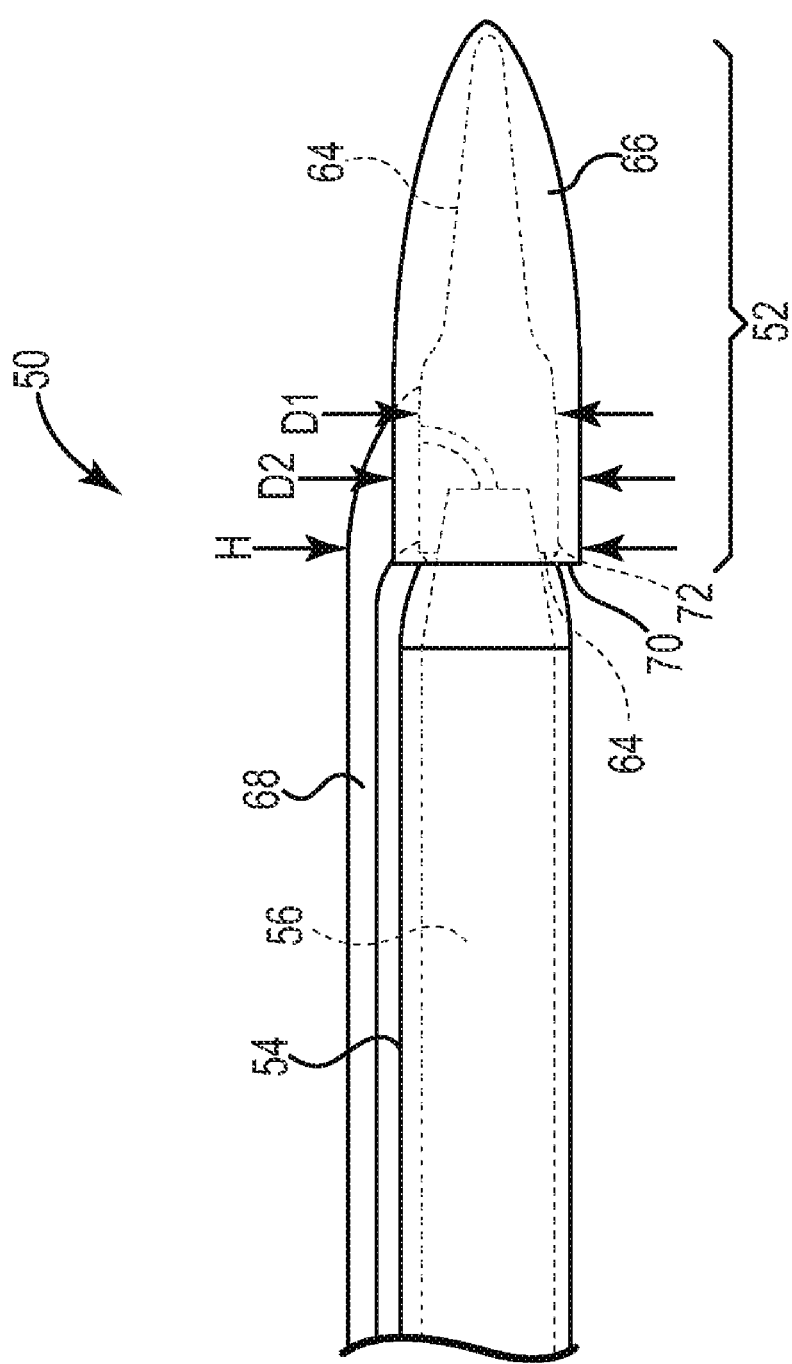
FIG. 5 is a side cross-sectional view of the tip sleeve attached to a tip core of the penile implant illustrated in FIG. 2.

FIG. 5 is a side cross-sectional view of the tip sleeve 66 attached to the tip core 64 of the penile implant 50. The tip core 64 has a circumferential groove formed around a periphery of its outer surface and the engagement ring 72 is coupled with the groove that is adjacent to the proximal end 62 of the inflatable bladder 54. Thus, in one embodiment the sleeve 66 is friction-fit to the tip core 64 and is retained by the engagement ring 72 that seats within the groove of the tip core 64.

In one embodiment, an interior surface of the sleeve 66 is coated with adhesive to allow the sleeve 66 to be adhesively attached to the tip core 64. In one embodiment, at least the interior surface of the sleeve 66 is formed of a material that is compatible with the tip core 64 to allow the sleeve 66 to be cohesively attached to the tip core 64.

The tip sleeve 66 increases the diameter of the tip core 64 from the diameter D1 to the diameter D2, which in this example is approximately 2T. For example, in the case where the thickness T is about 1 mm, the diameter D1 increases from 10 mm to the diameter D2 of 12 mm, and the overall length of the penile implant 50 increases in a minimal fashion by 1 mm. The tip sleeve 66 has a minimal or no effect on the length of the tip core 64. For example, the tip core 64 provides a first proximal tip length and the tip sleeve 66, when attached over the tip core 64, provides the tip assembly 52 with a second proximal tip length that is substantially the same (within 1-5 mm) as the first proximal tip length. In contrast, attachment of the rear tip extender 20 (FIG. 1) increases the length of implant by about 3 cm, or by a factor of about 30 over the tip sleeve 66.

An overall proximal height H of the rear tip assembly 52 is measured from an edge of the conduit 68 to an outside surface of the tip sleeve 66. In one embodiment, the conduit 66 is provided as a "zero angle" tubing and the proximal height H is about 18 mm for a thickness T of the tip sleeve 66 of about 1 mm.

Figure 6A:
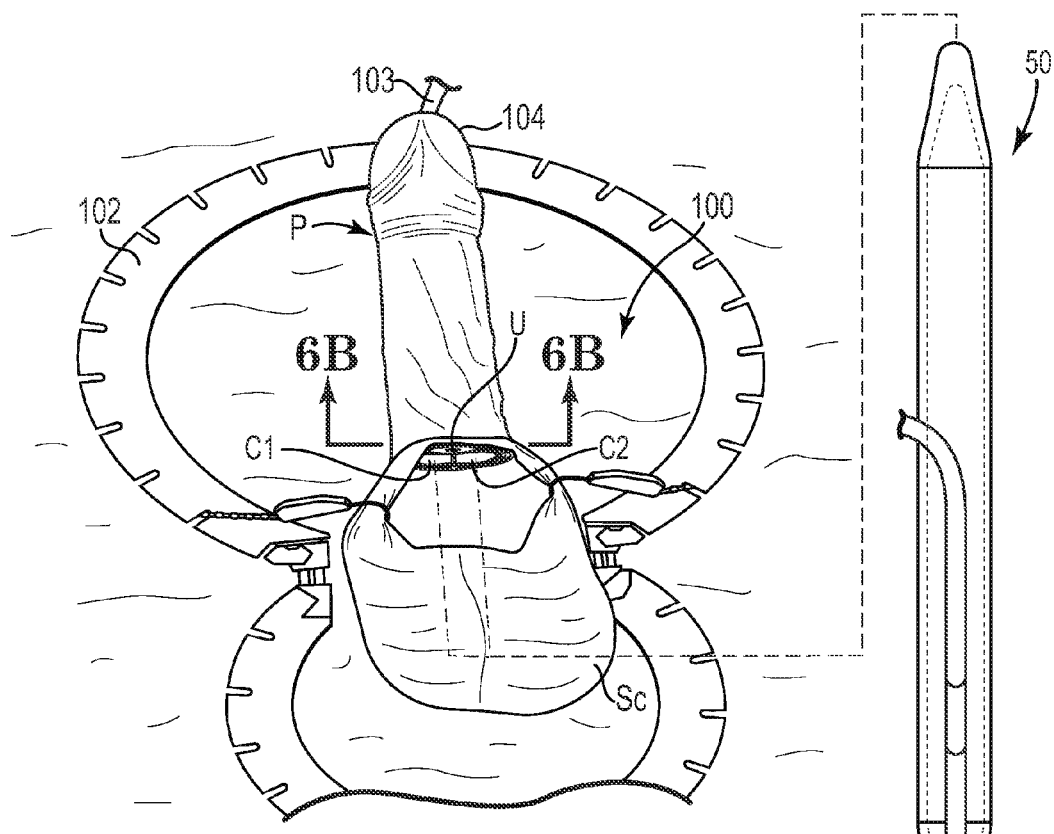
FIG. 6A is a top view and FIG. 6B is a cross-sectional view of a penis prepared to receive the penile implant illustrated in FIG. 2.
Figure 6B:
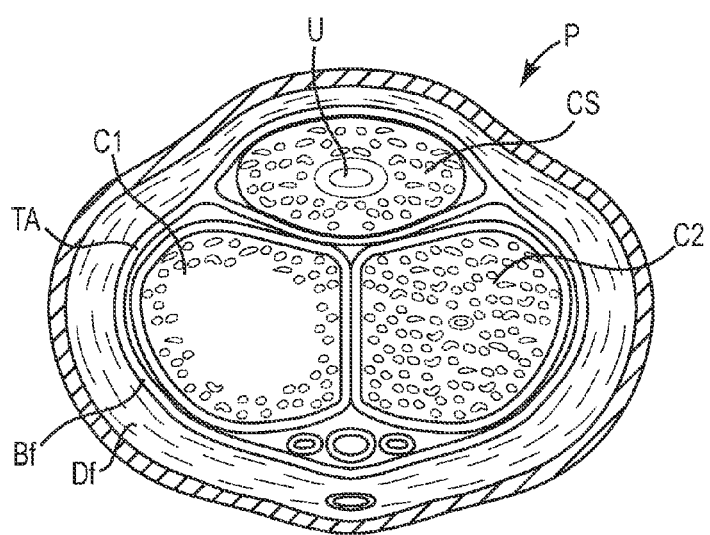

FIG. 6A is a top view and FIG. 6B is a cross-sectional view of a penis P prepared to receive the penile implant 50. The corpora cavernosa are illustrated as C1 and C2, where the corpora cavernosum C1 of FIG. 6B has been opened in a corporotomy procedure to a size that is suited to receive penile implant 50.

The groin area 100 of the patient is shaved, cleaned and suitably prepped with a surgical solution prior to draping with a sterile drape as directed by the healthcare provider's procedures. A retraction device, such as a retractor 102 sold under the trademark Lone Star and available from Lone Star Medical Products of Stafford, Tex., is placed around the penis P if so desired by the surgeon to establish a surgically clean field. A catheter 103 is inserted into the urethra U from the distal end 104 of the penis P. Thereafter, the surgeon forms an incision to access the corpora cavernosa C1 and C2 of the penis.

Suitable examples of incisions include either an infrapubic incision or a transverse scrotal incision. The infrapubic incision is initiated between the umbilicus and the penis (i.e., above the penis), whereas the transverse scrotal incision is made across an upper portion of the patient's scrotum Sc.

As an example of the transverse scrotal approach, with reference to FIG. 6B, the surgeon forms a 2-3 cm transverse incision through the subcutaneous tissue of the median raphe of the upper scrotum Sc and dissects down through the Darto's fascia Df and Buck's fascia Bf to expose the tunicae albuginea TA of the penis P. Thereafter, each corpora cavernosum C1 and C2 is exposed in a corporotomy where a small (approximately 1.5 cm) incision is formed through the tissue and the fascia to allow the surgeon to access and subsequently dilate the corpora cavernosa C1 and C2.

In the illustrated example, the penis P is reclined against the torso such that the urethra U, surrounded by corpus spongiosum tissue, is oriented upward. A corporotomy tool, for example a cavernatome (not shown), is introduced into the exposed the corpora cavernosa (C1 and C2) to remove (e.g., "core out") the corpora cavernosum C1 proximally and distally. With reference to both FIGS. 6A and 6B, the surgeon typically will insert a blunt-ended scissors or other elongated tool to separate a portion of the spongiosum material to open a pathway for the cavernatome. Thereafter, the cavernatome is manipulated within each corpora cavernosum C1 and C2 distally and proximally with sequentially larger diameters until the corporotomy provides an opening of about 10 mm.

A length of the corporotomy is measured from the crus of the penis proximately to a mid-glans location of the penis distally. The surgeon inserts the shaft of the cavernatome into the corporotomy to measure the proximal and distal length of each corpora cavernosum C1 and C2. For example, the shaft is inserted into one of the corpora cavernosa C1 or C2 forward in the distal penis toward the glans penis, the distal measurement is recorded, and the shaft is inserted into the same corpora cavernosum C1 or C2 rearward in the proximal penis toward the crus of the penis to record the proximal length of the corpora. The distal and proximal measurements would typically be made in reference to a "stay stitch" (not shown) temporarily placed in the incision. The sum of the distal and the proximal measurements represent the length of the corporotomy into which the implant 50 (FIG. 2) is placed. This procedure is repeated for the other of the corpora cavernosa C1 or C2 to measure the length of the companion corpora.

Different patients have different anatomy. Some patients will present with fibrotic proximal corpora that have a diameter that is narrower than a diameter of the remaining corporotomy. For example, some patients will have a penile implant that requires replacement. Upon removal (explant) of the penile implant the surgeon will discover that the proximal corporotomy toward the crus of the penis has become fibrotic and difficult to open.

With reference to FIG. 2 and FIG. 6, the implant 50 provides a first proximal tip diameter D2 that is suitable for implanting into a patient with an approximately uniform corporotomy. In addition, the implant 50 provides a removable tip sleeve 66 that can be removed to expose the tip core 64 having a second implantable proximal tip diameter D1 that is narrower than the first proximal tip diameter D2. The implant 50 thus provides the surgeon with a convertible proximal tip that can be converted between the larger first proximal tip diameter D2 and the smaller second proximal tip diameter D1. In this regard, the proximal tip assembly 52 has a delivered proximal tip diameter D2 (FIG. 2) and the tip sleeve 66 is removable from the tip core 64 to provide an implantable proximal tip diameter D1 that is smaller than the delivered proximal tip diameter D2. In one embodiment, the sleeve 66 provides means for converting the proximal tip assembly 52 to an implantable proximal tip diameter D1 that is smaller than the first/delivered proximal tip diameter D2 without significantly altering or increasing the length of the tip assembly 52.

Figure 6C:
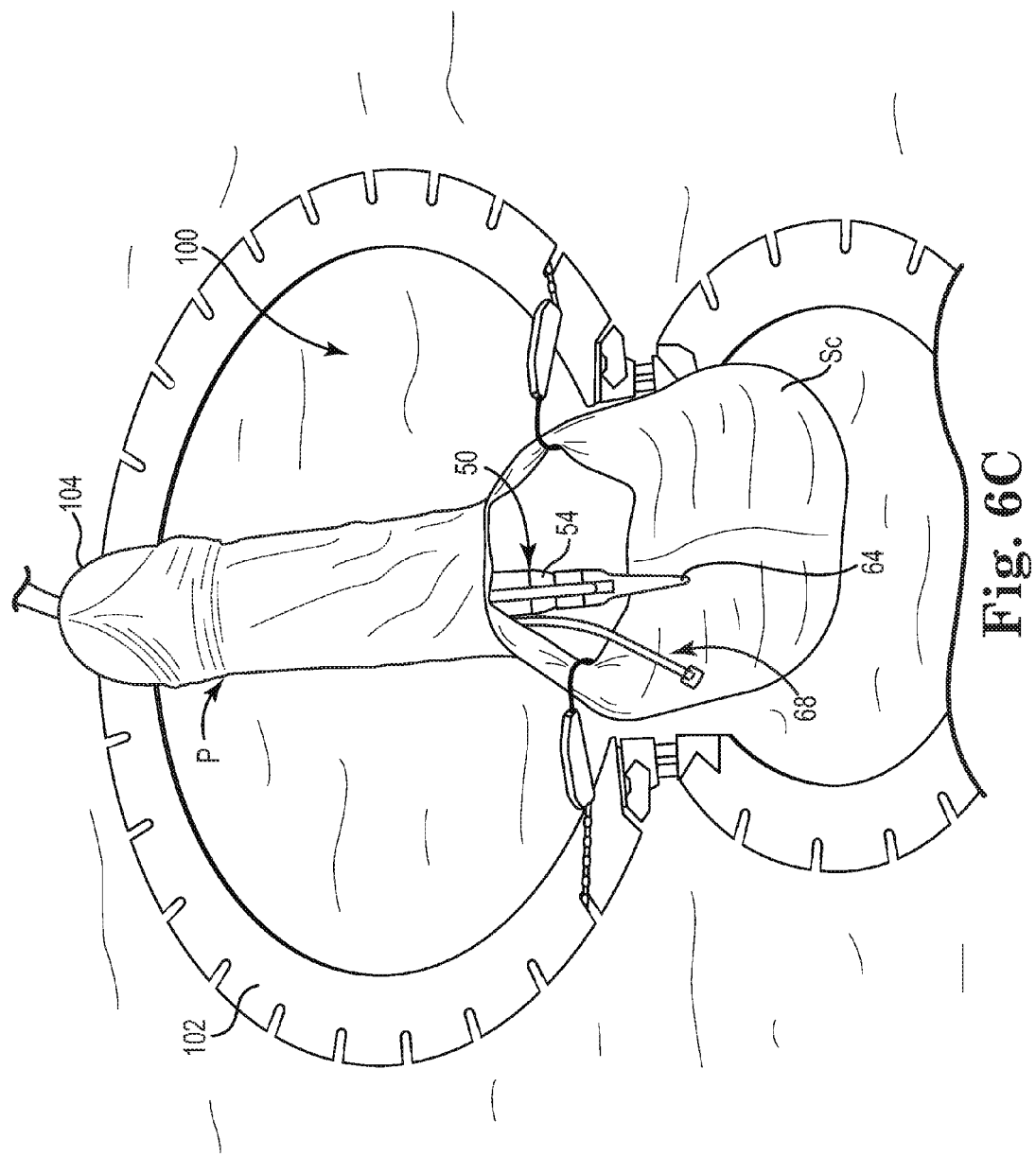
FIG. 6C is a top perspective view of the penile implant illustrated in FIG. 2 with the distal tip implanted into a corporotomy formed in the penis.

As illustrated in FIG. 6C, the sleeve 66 has been removed to expose the proximal tip core 64 having the narrower proximal tip diameter D1 that is configured to accommodate a patient with a narrower proximal corporotomy.

In one embodiment, a method of providing a patient having a predetermined corporotomy length with an implant having a length that is sized for the predetermined corporotomy length includes: providing a penile implant 50 having a delivered length that is approximately equal to the predetermined corporotomy length and having a distance that extends from a distal end of a distal tip 58 to a proximal end of a proximal tip assembly 52, the proximal tip assembly 52 providing a first proximal tip diameter D2; and reducing the first proximal tip diameter D2 to a smaller implantable proximal tip diameter D1.

After insertion of the implant 50 the corporotomy is closed and the remaining portions of the penile prosthetic device, for example a reservoir and/or a pump, are implanted in the abdomen and scrotum S, respectively, of the patient.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A method of providing a patient having a predetermined corporotomy length with an implant having a length that is sized for the predetermined corporotomy length, the method comprising:
    providing a penile implant having a length that is approximately equal to the predetermined corporotomy length and comprising a distance that extends from a distal end of a distal tip to a proximal end of a proximal tip assembly, the proximal tip assembly providing a first proximal tip diameter; and
    reducing the first proximal tip diameter to a smaller implantable proximal tip diameter by removing a tip sleeve of the proximal tip assembly and exposing a tip core of the proximal tip assembly while leaving the length of the penile implant substantially unchanged.

2. The method of claim 1, wherein removing a tip sleeve of the proximal tip assembly comprises peeling a tip sleeve that is adhesively attached to a tip core of the proximal tip assembly.

3. The method of claim 1, wherein removing a tip sleeve of the proximal tip assembly comprises peeling a tip sleeve that is cohesively attached to a tip core of the proximal tip assembly.

4. The method of claim 1, wherein removing a tip sleeve of the proximal tip assembly comprises detaching a distal end of a tip sleeve that is mechanically attached to a distal end of a tip core of the proximal tip assembly.

5. A method of claim 1, the method further comprising:
    forming a corporotomy in a corpora cavernosum of a penis; and
    determining a maximum width of a proximal corpora of the corporotomy formed in the penis.

* * * * *